(12) United States Patent
Sawa et al.

(10) Patent No.: US 8,849,588 B2
(45) Date of Patent: Sep. 30, 2014

(54) HARDNESS TEST METHOD AND PROGRAM

(75) Inventors: Takeshi Sawa, Kawasaki (JP); Eiji Furuta, Sagamihara (JP)

(73) Assignee: Mitutoyo Corporation, Kanagawa (JP)

( * ) Notice: Subject to any disclaimer, the term of this patent is extended or adjusted under 35 U.S.C. 154(b) by 435 days.

(21) Appl. No.: 13/226,687

(22) Filed: Sep. 7, 2011

(65) Prior Publication Data
US 2012/0101743 A1    Apr. 26, 2012

(30) Foreign Application Priority Data

Oct. 25, 2010  (JP) .................. 2010-238718

(51) Int. Cl.
  *G01N 3/48*  (2006.01)
  *G01N 3/42*  (2006.01)
(52) U.S. Cl.
  CPC .......... *G01N 3/42* (2013.01); *G01N 2203/0208* (2013.01); *G01N 2203/0218* (2013.01)
  USPC .............................................. 702/41; 73/81
(58) Field of Classification Search
  USPC ............. 702/33–35, 41–43; 73/78, 81, 82, 86
  See application file for complete search history.

(56) References Cited

U.S. PATENT DOCUMENTS

| | | | |
|---|---|---|---|
| 4,719,583 A | 1/1988 | Takafuji et al. | |
| 5,999,887 A | 12/1999 | Giannakopoulos et al. | |
| 2006/0042362 A1 | 3/2006 | Hayashi et al. | |
| 2007/0113628 A1 | 5/2007 | Miyahara | |
| 2008/0033665 A1* | 2/2008 | Beghini et al. | 702/42 |
| 2008/0141782 A1* | 6/2008 | Kim | 73/823 |
| 2009/0044609 A1 | 2/2009 | Sawa et al. | |

FOREIGN PATENT DOCUMENTS

JP      2009-047427      3/2009

OTHER PUBLICATIONS

Search report from E.P.O, mail date is Apr. 19, 2013.

* cited by examiner

*Primary Examiner* — Manuel L Barbee
(74) *Attorney, Agent, or Firm* — Greenblum & Bernstein, P.L.C.

(57) ABSTRACT

A hardness test method performed by a controller of a hardness tester includes a first measurement process measuring an indentation curve (indentation history curve) for a plurality of times under a same condition with respect to a test specimen for verification in a predetermined environment; a setting process setting an acceptable range of variation in a load loading curve based on load loading curves (load loading history curves) of the plurality of the indentation curves obtained by the first measurement process; a second measurement process measuring an indentation curve under a same condition as the first measurement process with respect to the test specimen in an actual usage environment; and a judging process judging whether a load loading curve of the indentation curve measured by the second measurement process is within the acceptable range of variation in a load loading curve set by the setting process.

19 Claims, 9 Drawing Sheets

HARDNESS TEST METHOD AND PROGRAM

CROSS-REFERENCE TO RELATED APPLICATIONS

The present application claims priority under 35 U.S.C. §119 of Japanese Application No. 2010-238718, filed on Oct. 25, 2010, the disclosure of which is expressly incorporated by reference herein in its entirety.

BACKGROUND OF THE INVENTION

1. Field of the Invention

The present invention relates to a hardness test method and a program.

2. Description of Related Art

Conventionally, as a material tester, a test method called an instrumented indentation test (nano-indentation test) is known in which, during a process of forming an indentation by pressing an indenter loaded with a predetermined load against a surface of a test specimen, a test force (force loaded on the indenter) and an indentation depth (amount of displacement of the indenter) are continuously measured, and a mechanical property of the material is determined by analyzing an obtained indentation curve (for example, see Japanese Patent Laid-Open Publication No. 2009-47427).

For an instrumented indentation test like this, to what extent a test can be performed at a small indentation depth without being influenced by a disturbance is important in evaluating performance of a tester. For example, fused silica (silica glass) is often used to perform a performance evaluation test. However, silica glass is less susceptible to disturbance due to its high elastic deformability in a small indentation range, so that a result of a performance evaluation test using silica glass may not be applicable to an actual installation environment. Thus, in general, as a verification method of an installation environment of an instrumented indentation tester, measurement of floor vibration is used.

However, an instrumented indentation test may be influenced not only by floor vibration but also by noise in an installation room and wind due to air conditioning and the like. Further, with respect to the floor vibration, its impact varies widely depending on the frequency of the vibration, and thus cannot be judged based on only a numeric value indicated by a vibration meter. Therefore, as it stands now, an experiment is conducted after performing, for example, inspection of an indenter, measurement of floor vibration, and the like that can be done, and validity of an obtained test result is judged based on empirical values.

SUMMARY OF THE INVENTION

A purpose of the present invention is to provide a hardness test method and a program that are capable of quantitatively verifying influence of an installation environment.

To achieve the above purpose, one aspect of the present invention is a hardness test method performed by a controller of a hardness tester. The hardness test method includes a first measurement process forming an indentation by pressing an indenter loaded with a predetermined load with respect to a test specimen for verification in a predetermined environment, and measuring for a plurality of times under a same condition an indentation history curve detecting an amount of displacement of the indenter and a test force loaded on the indenter during the formation of the indentation; a setting process setting an acceptable range of variation in load loading history curves based on load loading history curves, formed during load loading of the plurality of the indentation history curves obtained by the first measurement process; a second measurement process measuring an indentation history curve under a same condition as the first measurement process with respect to the test specimen for verification in an actual usage environment; and a judging process judging whether a load loading history curve of the indentation history curve measured by the second measurement process is within the acceptable range of variation in a load loading history curve set by the setting process.

According to another aspect of the present invention, in the hardness test method, the indenter is a cone-shaped indenter. The setting process includes fitting the load loading history curves of the plurality of the indentation history curves using quadratic functions; selecting two curves having maximum and minimum slope values; and setting a range between the two selected curves as the acceptable range of variation in the load loading history curve.

According to another aspect of the present invention, in the hardness test method, the slope values of the two selected curves are multiplied by a safety factor to set the acceptable range of variation in the load loading history curve.

According to another aspect of the present invention, in the hardness test method, the indenter is a cone-shaped indenter. The setting process includes fitting the load loading history curves of the plurality of the indentation history curves using quadratic functions; calculating a correlation coefficient; and setting a minimum of the calculated correlation coefficient or above as the acceptable range of variation in the load loading history curve.

According to another aspect of the present invention, in the hardness test method, the minimum of the calculated correlation coefficient is multiplied by a safety factor to set the acceptable range of variation in the load loading history curve.

According to another aspect of the present invention, the hardness test method further includes an estimation process estimating a type of disturbance in the actual usage environment based on the indentation history curve measured by the second measurement process.

According to another aspect of the present invention, in the hardness test method, the test specimen for verification is copper, aluminum, or gold.

Another aspect of the present invention is a program that causes a computer to act as a first measurer forming an indentation by pressing an indenter loaded with a predetermined load with respect to a test specimen for verification in a predetermined environment, and measuring for a plurality of times under a same condition an indentation history curve detecting an amount of displacement of the indenter and a test force loaded on the indenter during the formation of the indentation; a setter setting an acceptable range of variation in load loading history curves based on the load loading history curves, formed during load loading, of the plurality of the indentation history curves obtained by the first measurer; a second measurer measuring an indentation history curve under a same condition as the first measurer with respect to the test specimen for verification in an actual usage environment; and a judger judging whether a load loading history curve of the indentation history curve measured by the second measurer is within the acceptable range of variation in a load loading history curve set by the setter.

According to the present invention, the hardness test method includes a first measurement process forming for a plurality of times under a same condition an indentation by pressing an indenter loaded with a predetermined load with respect to a test specimen for verification in a predetermined environment, and measuring for a plurality of times under a same condition an indentation history curve detecting an amount of displacement of the indenter and a test force loaded on the indenter during the formation of the indentation; a setting process setting an acceptable range of variation in load loading history curves based on the load loading history curves, formed during load loading, of the plurality of the indentation history curves obtained by the first measurement process; a second measurement process measuring an indentation history curve under a same condition as the first measurement process with respect to the test specimen for verification in an actual usage environment; and a judging process judging whether a load loading history curve of the indentation history curve measured by the second measurement process is within the acceptable range of variation in a load loading history curve set by the setting process. Therefore, after a measurement is performed with respect to the test specimen for verification in the predetermined environment and an acceptable range of variation in the load loading curves is set, the same measurement is performed with respect to the same test specimen for verification in an actual usage environment; and, based on whether the obtained load loading history curve is within the set acceptable range, whether the influence of disturbance in the actual usage environment is large can be determined. Therefore, the influence of an installation environment can be quantitatively verified.

BRIEF DESCRIPTION OF THE DRAWINGS

The present invention is further described in the detailed description which follows, in reference to the noted plurality of drawings by way of non-limiting examples of exemplary embodiments of the present invention, in which like reference numerals represent similar parts throughout the several views of the drawings, and wherein.

DETAILED DESCRIPTION OF THE INVENTION

The particulars shown herein are by way of example and for purposes of illustrative discussion of the embodiments of the present invention only and are presented in the cause of providing what is believed to be the most useful and readily understood description of the principles and conceptual aspects of the present invention. In this regard, no attempt is made to show structural details of the present invention in more detail than is necessary for the fundamental understanding of the present invention, the description is taken with the drawings making apparent to those skilled in the art how the forms of the present invention may be embodied in practice.

In the following, with reference to the drawings, a hardness test method according to the present invention is explained in detail. The hardness test method according to the present invention is performed for verifying whether influence of disturbance is large with respect to an installation environment (actual usage environment) of a hardness tester when performing a hardness test. The hardness tester according to the present invention is a hardness tester having a function for using the hardness test method.

First Embodiment

Figure 1:
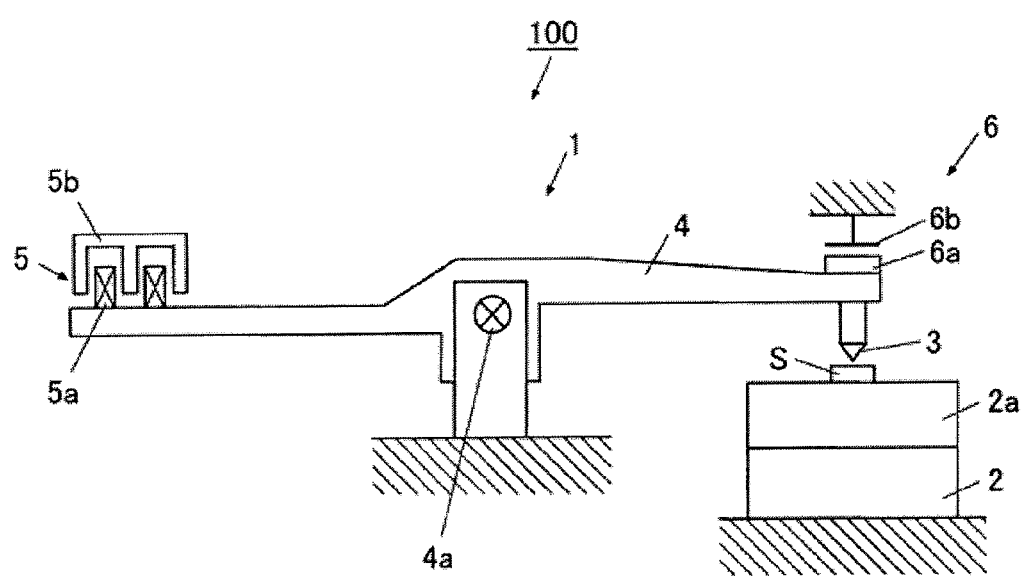
FIG. 1 is a schematic diagram illustrating a hardness tester according to the present invention.
Figure 2:
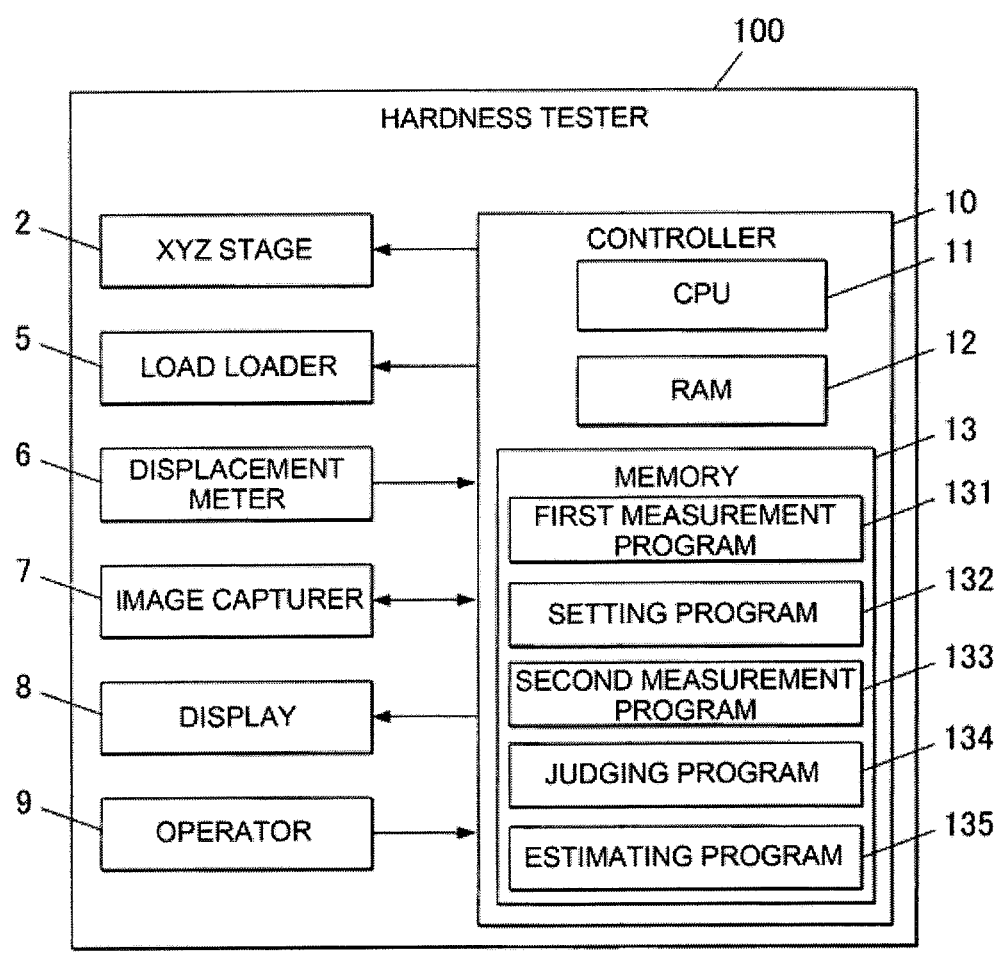
FIG. 2 is a block diagram illustrating a control configuration of a hardness tester according to a first embodiment.

A hardness tester 100 according to the present embodiment is an instrumented indentation tester capable of continuously monitoring a test force applied to an indenter 3 and an indentation depth of the indenter 3. The hardness tester 100 includes, for example, as FIGS. 1 and 2 illustrate, a controller 10 and a hardness tester body 1 in which component members are arranged. The tester body 1 is configured to include an XYZ stage 2 moving a test specimen S in X, Y, and Z directions; a load lever 4 having on one end thereof the indenter 3 forming an indentation on the test specimen S; a load loader 5 loading (applying) a predetermined load (test force) to the load lever 4; a displacement meter 6 detecting an amount of displacement of the indenter 3; an image capturer 7 capturing an image of an indentation formed on a surface of the test specimen S and the like; a display 8; an operator 9; and the like.

The XYZ stage 2 is configured to move in the X, Y, and Z directions (that is, horizontal and vertical directions) according to a control signal input from the controller 10. The test specimen S is moved back and forth, left and right, and up and down by the XYZ stage 2 so as to adjust a location relative to the indenter 3. The XYZ stage 2 holds the test specimen S using a test specimen holding stage 2a so as to keep the test specimen S mounted on an upper surface thereof in alignment during a test measurement. Here, the test specimen S is a test specimen for verification that can be favorably used in the hardness test method according to the present embodiment. For example, a plastically easily deformable metallic material such as copper, aluminum, gold, and the like is used.

As the indenter 3, for example, a cone-shaped indenter can be used, such as a Vickers pyramid indenter (face angle is 136±0.5°), a Berkovich triangular pyramid indenter (angle between one face and an indenter axis is 65.03° or 65.27°), a conical indenter (apex angle is 120±0.35° and the like), a Knoop rhombic-base pyramid indenter (apical angles between opposite faces are 172°30' and 130°, and the like. When such an indenter 3 is loaded with a predetermined load and is pressed against a surface of the test specimen S, an indentation is formed on the surface of the test specimen S.

The load lever 4, for example, is formed in an approximately rod shape, and is fixed on a seating via a cross spring 4a near its center. On one end of the load lever 4, the indenter 3 is provided, which is freely movable above the test specimen S both toward and away from the test specimen S, and which is pressed against a surface of the test specimen S to form an indentation, the test specimen S being mounted on the test specimen holding stage 2a. On the other end of the load lever 4, force coils 5a are provided, which constitute the load loader 5.

The load loader 5, for example, is a force motor, and is configured to include the force coils 5a attached to the load lever 4; a fixed magnet 5b fixed so as to face the force coils 5a; and the like. The load loader 5, for example, rotates the load lever 4 according to a control signal input from the controller 10, using as a driving force a force generated by electromagnetic induction of a magnetic field created in a gap by the fixed magnet 5b and an electrical current flowing in the force coils 5a provided in the gap. This allows the end of the load lever 4 on the indenter 3 side to tilt downwardly so as to press the indenter 3 against the test specimen S.

The displacement meter 6, for example, is a capacitive displacement sensor, and is configured to include a movable electrode plate 6a provided on the end of the load lever 4 on the indenter 3 side, and a fixed electrode plate 6b fixed so as to face the movable electrode plate 6a. The displacement meter 6, for example, detects an amount of displacement that the indenter 3 moved when forming an indentation on the test specimen S (indentation depth when the indenter 3 is pressed against the test specimen S) by detecting a change in a capacitance between the movable electrode plate 6a and the fixed electrode plate 6b, and outputs a displacement signal based on the detected amount of displacement to the controller 10. As the displacement meter 6, the capacitive displacement sensor is used as an example. However, it is not limited to this. For example, it may also be an optical displacement sensor or an eddy current displacement sensor.

The image capturer 7 includes, for example, a camera and the like, and captures, for example, an image of an indentation formed on the surface of the test specimen S by the indenter 3, and the like, above the test specimen holding stage 2a, according to a control signal input from the controller 10.

The display 8, for example, is a liquid crystal display panel, and performs display processing of a surface image of the test specimen S captured by the image capturer 7, various test results, and the like, according to a control signal input from the controller 10.

The operator 9, for example, is a group of operation keys such as a keyboard and the like, and, when operated by a user, outputs an operation signal associated with the operation to the controller 10. Further, the operator 9 may also include a pointing device such as a mouse, a touch panel, and the like, a remote controller, and the like, and other operation devices. The operator 9 is operated when a user performs directive input for performing a hardness test with respect to the test specimen S, when setting a test force, that is, a load, loaded on the indenter 3, and the like.

The controller 10 is configured to include a CPU (Central Processing Unit) 11, a RAM (Random Access Memory) 12, a memory 13, and the like, and is connected, via a system bus, to the XYZ stage 2, the load loader 5, the displacement meter 6, the image capturer 7, the display 8, the operator 9, and the like.

The CPU 11, for example, performs various control processing according to various processing programs for a hardness tester stored in the memory 13.

The RAM 12, for example, includes a program storage area for deploying a processing program and the like executed by the CPU 11; a data storage area storing input data and a processing result and the like generated when a processing program is executed; and the like.

The memory 13, for example, stores a system program executable on the hardness tester 100; various processing programs executable under the system program; data used when the various processing programs are executed; data of various processing results arithmetically processed by the CPU 11; and the like. A program is stored in the memory 13 in the form of computer readable program code.

Specifically, the memory 13 stores, for example, a first measurement program 131, a setting program 132, a second measurement program 133, a judging program 134, an estimating program 135, and the like.

The first measurement program 131, for example, is a program that causes the CPU 11 to form an indentation by pressing the indenter 3 loaded with a predetermined load with respect to the test specimen S in a predetermined environment, and measure for multiple times under a same condition an indentation history curve (indentation curve) detecting an amount of displacement (indentation depth (h)) of the indenter 3 and a test force (F) loaded on the indenter 3 during the formation of the indentation.

Figure 3A:
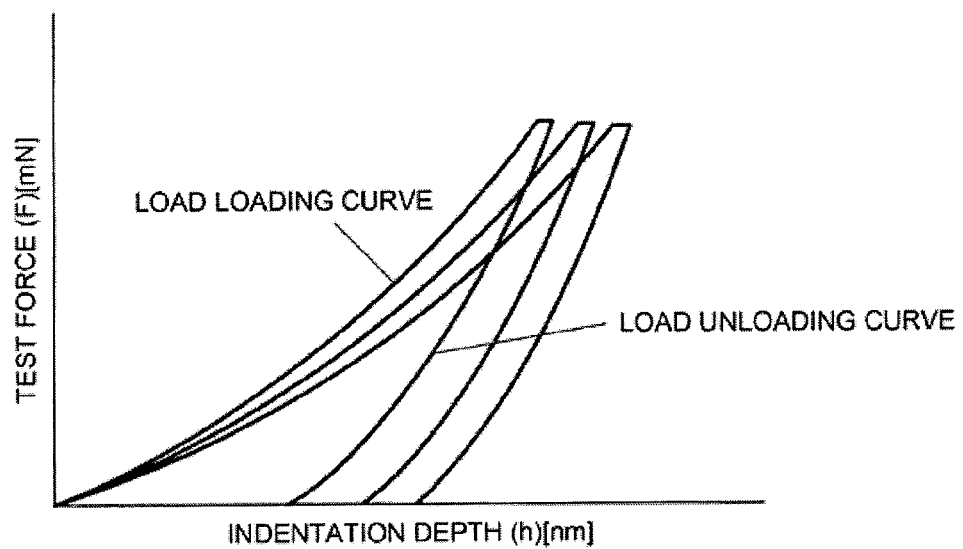
FIG. 3(a) is an example illustrating an indentation history curve measured by a first measurement process.

Here, the predetermined environment is a nearly ideal environment in which various disturbances that interfere with measurement are nearly absent, the various disturbances including sudden vibrations such as opening and closing of a door, operation sound of a machine, falling sound, and the like; relatively high frequency disturbance of the order of several 100 Hz such as voice and the like; relatively low frequency disturbance such as wind and the like; and the like. A user installs the hardness tester 100 in such a predetermined environment and performs measurement. When a user performs a directive input with respect to the operator 9 for performing a hardness test with respect to the test specimen S, in response to this, the CPU 11 executes the first measurement program 131, performs the instrumented indentation test with respect to the test specimen S in the predetermined environment, and performs measurement of a test force (F) versus indentation depth (h) curve (indentation curve) (the first measurement process). The instrumented indentation test in this first measurement process is performed for multiple times under a same test condition. It is desirable that the indentation depth (h) be as small as possible for ease of confirming the influence of an installation environment. For example, it is desirable that the indentation depth (h) be 100 nm or less. The number of tests is set by a user in advance. FIG. 3(a) is an example illustrating an indentation curve measured by the first measurement process.

Specifically, for the measurement of the test force (F) versus indentation depth (h) curve (indentation curve), each time the following process is performed. First, after the test specimen S is mounted on the test specimen holding stage 2a, when an operation signal is input from the operator 9 instructing the CPU 11 to perform measurement, the CPU 11 controls the load loader 5 to apply a predetermined test force to the test specimen S. Then, the CPU 11 continuously measures an indentation depth (h) [nm] of the indenter 3 on the test specimen S during formation of an indentation and a test force (F) [mN] during the formation of the indentation to measure a test force (F) versus indentation depth (h) curve.

More specifically, when the test specimen S is mounted on the test specimen holding stage 2a and an operation signal is input, the CPU 11 outputs a control signal to the load loader 5, and uses as a driving force a force generated by electromagnetic induction of a magnetic field created in a gap by the fixed magnet 5b of the load loader 5 and an electrical current flowing in the force coils 5a provided in the gap, to rotate the load lever 4. Thereby, the end of the load lever 4 on the indenter 3 side tilts downwardly to allow the indenter 3 to form an indentation on the test specimen S. During the formation of the indentation, the load loaded on the indenter 3 is gradually increased until a set maximum test force is reached (load loading process). In this load loading process, as a load loading history curve (load loading curve) in FIG. 3(a) illustrates, by increasing the test force loaded on the indenter 3, the indentation depth of the indenter 3 on the test specimen S also increases. The indenter 3 is a cone-shaped indenter. Therefore, the load loading history curve is a quadratic curve. Next, when the CPU 11 judges that the load loaded on the indenter 3 has reached the maximum test force, the CPU 11 operates the load loader 5 by controlling supply of the electrical current to the driving coils to gradually decrease the load loaded on the indenter 3 (load unloading process). In the load unloading process, as a load unloading curve in FIG. 3(a) illustrates, by decreasing the test force loaded on the indenter 3, the indentation depth of the indenter 3 on the test specimen S also decreases.

By executing such a first measurement program 131, the CPU 11 acts as a first measurer (also referred to as a "first scale").

Figure 3B:
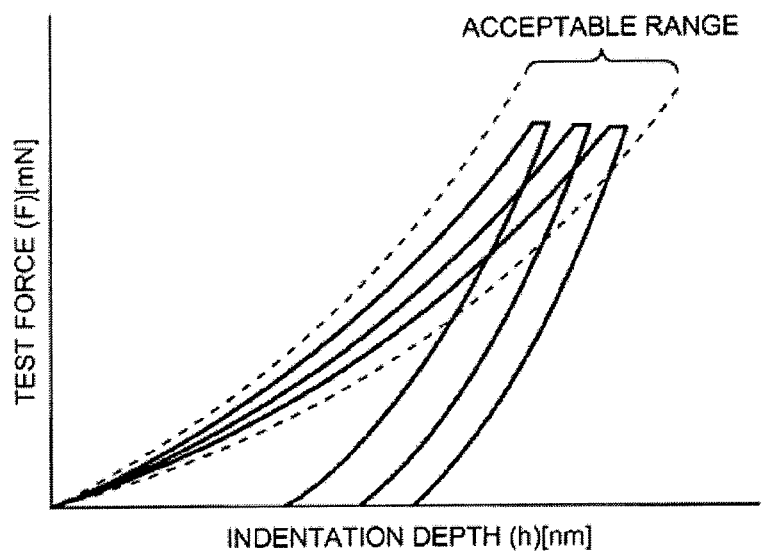
FIG. 3(b) is an example illustrating an acceptable range set by a setting process.

The setting program 132, for example, is a program that causes the CPU 11 to set a predetermined acceptable range of variation in load loading history curves (load loading curves) based on the load loading history curves (load loading curves), formed during load loading, of the plurality of the indentation history curves (indentation curves) obtained by executing the first measurement program 131. Specifically, first, the CPU 11 perceives the shape of the load loading history curves of the plurality of the indentation history curves obtained by executing the first measurement program 131. In the present embodiment, it is perceived that the load loading history curves are quadratic curves. Next, the CPU 11 uses quadratic functions to fit the load loading curves of the plurality of the indentation curves obtained by executing the first measurement program 131 to select two curves having maximum and minimum slope values, and sets a range between the two selected curves as a predetermined acceptable range of variation in a load loading curve (setting process). Here, the acceptable range of variation in a load loading curve is a range specifying an acceptable measurement error range in a case where a measurement is performed with respect to the test specimen S, which is a test specimen for verification, under the same test condition as that for the above described first measurement process. That is, in the case where the installation environment of the hardness tester 100 is changed and a measurement is performed with respect to the test specimen S under the same test condition as that for the first measurement process, when a load loading curve is within the acceptable range, the installation environment can be judged as being close to the predetermined environment, having small influence of disturbance. At this time, it is also possible to multiply by a predetermined safety factor the slope values of the two curves selected by fitting the above described load loading curves using quadratic functions to set an acceptable range of variation in a load loading curve. For example, by performing operations of a maximum slope value×2 and a minimum slope value×½, an acceptable range is set. For the safety factor, values set by a user in advance are used. This allows adding a certain degree of margin to a set acceptable range. FIG. 3(b) is an example illustrating an acceptable range set by the setting process. By executing such a setting program 132, the CPU 11 acts as a setter.

Figure 4A:
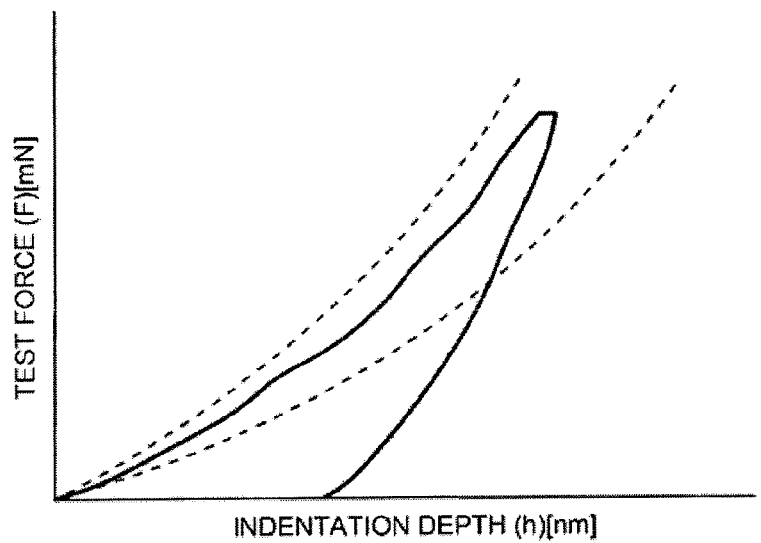
FIG. 4(a) is an example in which a load loading history curve measured in an actual usage environment is within an acceptable range.
Figure 4B:
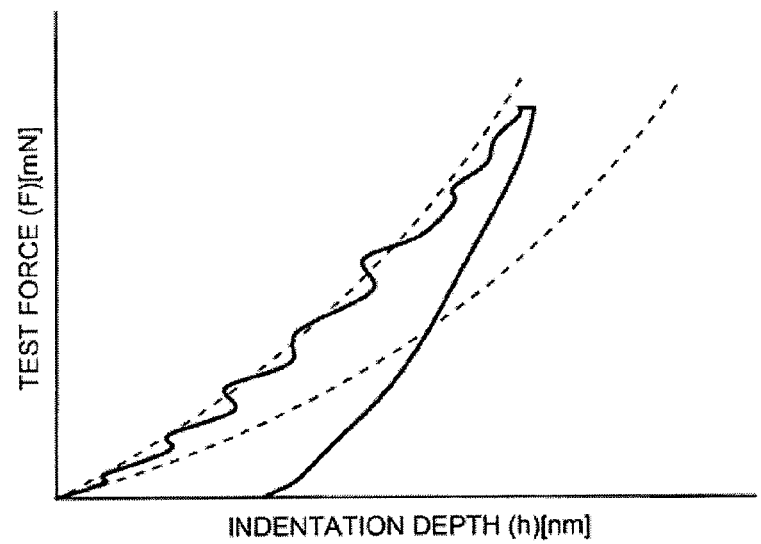
FIG. 4(b) is an example in which a load loading history curve measured in an actual usage environment is outside an acceptable range.

The second measurement program 133, for example, is a program that causes the CPU 11 to measure an indentation history curve (indentation curve) under the same condition as that for the first measurement program 131 (first measurement process) with respect to the test specimen S in an actual usage environment. Here, the actual usage environment is an actual installation environment of the hardness tester 100. As compared to the nearly ideal predetermined environment, the actual usage environment is an environment susceptible to various disturbances. A user moves the hardness tester 100 from the predetermined environment where the first measurement process was performed to such an actual usage environment, and performs a measurement. When a user performs a directive input with respect to the operator 9 to perform a hardness test with respect to the test specimen S, in response to this, the CPU 11 executes the second measurement program 133, and performs the same control as during the execution of the above-described first measurement program 131 to measure an indentation curve in the actual usage environment (the second measurement process). FIGS. 4(a) and 4(b) are each an example illustrating a load loading curve of an indentation curve obtained as a result. FIG. 4(a) illustrates an example in which a load loading curve is within an acceptable range. FIG. 4(b) illustrates an example in which a load loading curve is outside an acceptable range. By executing such a second measurement program 133, the CPU 11 acts as a second measurer (also referred to as a "second scale").

The judging program 134, for example, is a program that causes the CPU 11 to judge whether a load loading history curve (load loading curve) of an indentation history curve (indentation curve) measured by executing the second measurement program 133 is within an acceptable range of variation in a load loading history curve (load loading curve) set by the setting program 132. Specifically, the CPU 11 judges whether a part of or the whole of a load loading curve measured in an actual usage environment is within a set acceptable range (judging process). Then, for example, the CPU 11 displays a message and the like on the display 8 to inform a user of a judged result. According to the judged result, the user can recognize whether the influence of disturbance is large or small with respect to the actual usage environment. That is, in a case where the whole of a load loading curve measured in the actual usage environment is within the acceptable range, it can be recognized as that the influence of disturbance is small; and in a case where even a part is not within the acceptable range, it can be recognized as that there was influence of some kind of disturbance. By executing such a judging program 134, the CPU 11 acts as a judger.

Figure 5A:
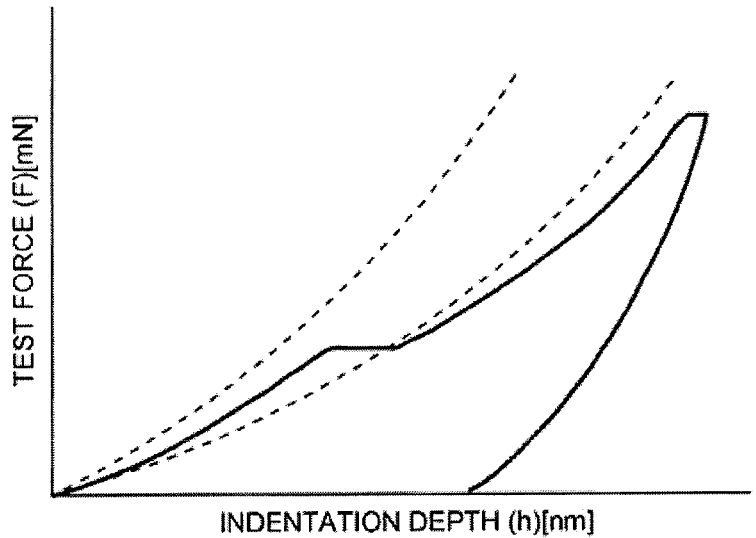
FIG. 5(a) is an example of an indentation history curve which shows a rapid change in displacement during indentation.
Figure 5B:
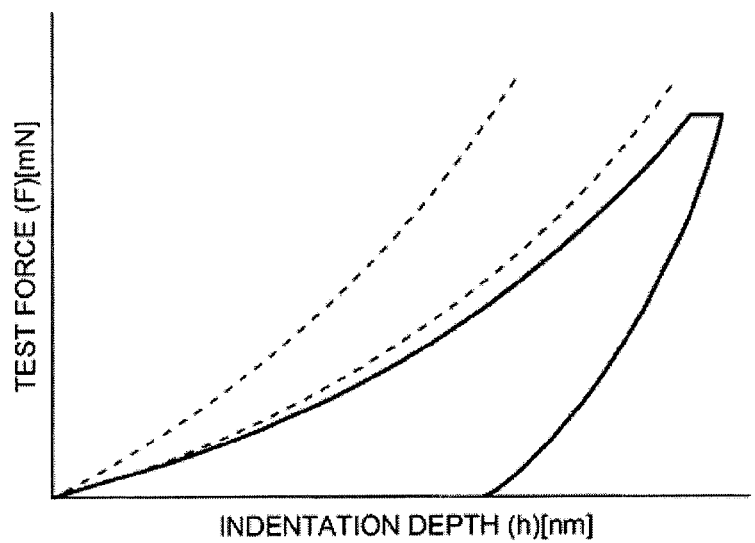
FIG. 5(b) is an example of an indentation history curve which, as a whole, shows large displacement.
Figure 5C:
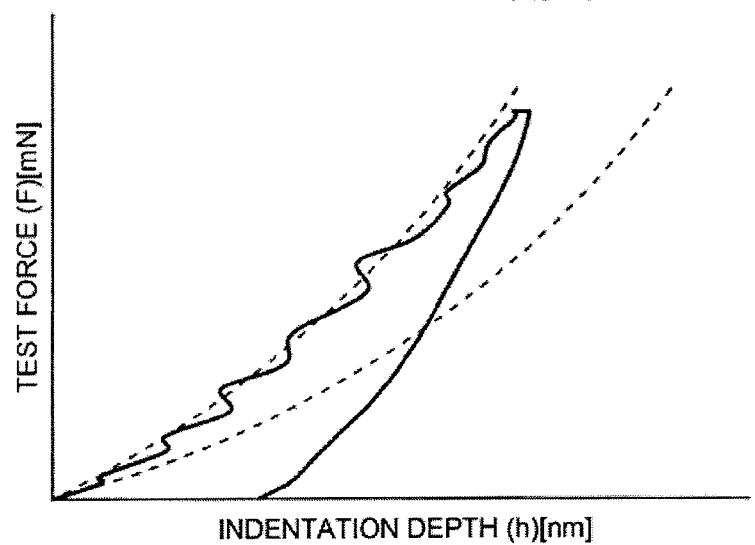
FIG. 5(c) is an example of an indentation history curve in which fluctuation is observed.

The estimating program 135, for example, is a program that causes the CPU 11 to estimate a type of disturbance in the actual usage environment based on the indentation curve (indentation history curve) measured by executing the second measurement program 133. Specifically, for example, the CPU 11 estimates a type of disturbance by comparing a shape of the indentation curve (behavior of the indentation curve) measured by the second measurement process with types of disturbance stored in advance (estimation process). The estimation process can be performed not only in the case where it is judged based on the result of the judging process that the influence of disturbance is large, but also in the case where it is judged that the influence of disturbance is small. That is, regardless the degree of the influence of disturbance, in a case where the shape of the indentation curve is disturbed, the type of disturbance in the installation environment can be estimated. For example, as FIG. 5(a) illustrates, in a case of an indentation curve in which displacement rapidly changes during indentation, it is estimated that a sudden vibration has occurred (load has changed in a case of a displacement controlled tester) such as opening and closing of a door, an operation sound of a machine, a falling sound, and the like. As FIG. 5(b) illustrates, in a case of an indentation curve in which large displacement appears, it is estimated that a relatively high frequency disturbance of the order of several 100 Hz such as a voice that does not appear as fluctuation of the curve has constantly occurred. As FIG. 5(c) illustrates, in a case of an indentation curve in which fluctuation appears, it is estimated that a relatively low frequency disturbance has been constantly shaking the tester. By executing such an estimation program 135, the CPU 11 acts as an estimator.

Figure 6:
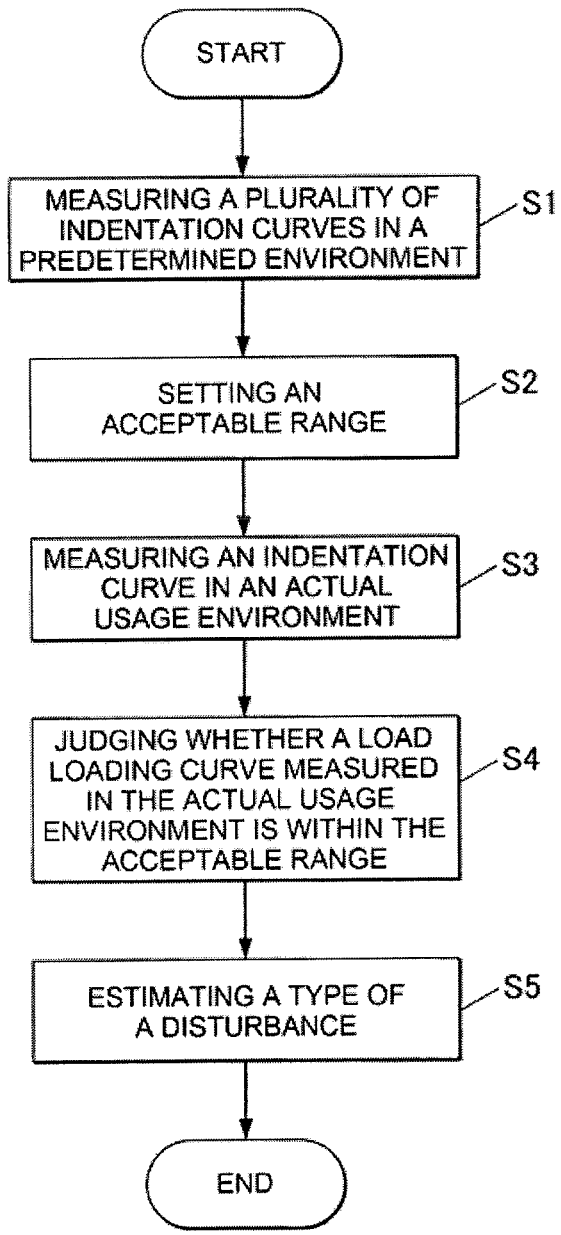
FIG. 6 is a flowchart for explaining a hardness test method according to the present invention.

FIG. 6 is a flowchart illustrating a hardness test method using the hardness tester 100. The following step S1 and step S2 are performed in a state in which the hardness tester 100 is installed in a predetermined environment, and step S3-step S5 are performed in a state in which the hardness tester 100 has been moved to an actual usage environment.

First, at step S1, in response to an operation of the operator 9, the CPU 11 executes the first measurement program 131, and measures a plurality of indentation curves with respect to the test specimen S in the predetermined environment (first measurement process). Next, at step S2, the CPU 11 executes the setting program 132, and sets an acceptable range of variation in load loading curves based on load loading curves of the plurality of the indentation curves obtained by the first measurement process (setting process).

Next, at step S3, the CPU 11 executes the second measurement program 133, and measures an indentation curve under the same condition as the first measurement process with respect to the test specimen S in the actual usage environment (second measurement process). Next, at step S4, the CPU 11 executes the judging program 134, and judges whether a load loading curve of the indentation curve measured by the second measurement process is within the acceptable range set by the setting process (judging process). Next, at step S5, the CPU 11 estimates a type of a disturbance (estimation process), and terminates processing.

As describe above, the hardness test method according to the present embodiment includes the first measurement process measuring an indentation curve for a plurality of times under the same condition with respect to the test specimen S in the predetermined environment (step S1); the setting process setting an acceptable range of variation in load loading curves based on the load loading curves of the plurality of the indentation curves obtained by the first measurement process (step S2); the second measurement process measuring an indentation curve under the same condition as the first measurement process with respect to the test specimen S in an actual usage environment (step S3); and the judging process judging whether the load loading curve of the indentation curve measured by the second measurement process is within the acceptable range of variation in a load loading curve set by the setting process (step S4). Therefore, after a measurement is performed with respect to the test specimen S in the predetermined environment and an acceptable range of variation in a load loading curve is set, the same measurement is performed with respect to the same test specimen S in an actual usage environment, and, based on whether the obtained load loading curve is within the set acceptable range, whether the influence of disturbance in the actual usage environment is large can be determined. Therefore, for example, the influence of an installation environment that cannot be determined by measurement of floor vibration alone can be quantitatively verified.

According to the hardness test method of the present embodiment, the indenter 3 is a cone-shaped indenter. In the setting process (step S2), the load loading curves of the plurality of the indentation curves are fitted using quadratic functions; two curves having maximum and minimum slope values are selected; and the range between the two selected curves is set as an acceptable range of variation in a load loading curve. Therefore, an acceptable range of variation in a load loading curve that can be used as a reference during a test in an actual usage environment is set from two load loading curves having maximum and minimum slope values obtained by the first measurement process.

Further, according to the hardness test method of the present embodiment, an acceptable range of variation in a load loading curve is set by multiplying the slope values of the two selected curves by a safety factor. Therefore, a certain degree of margin can be added to a set acceptable range, which allows an unexpected measurement error in an actual usage environment to be absorbed.

The hardness test method of the present embodiment further includes an estimation process (step S5) estimating a type of a disturbance in an actual usage environment based on the indentation curve measured by the second measurement process (step S3). Therefore, what type of disturbance is occurring can be estimated from the behavior of the indentation curve measured in the actual usage environment. This allows a user to easily take measures to reduce the disturbance.

According to the hardness test method of the present embodiment, the test specimen S is copper, aluminum, or gold. Therefore, a measurement is performed using the test specimen S that is susceptible to plastic deformation and for which the influence of disturbance is easy to appear in an indentation curve, and thus a more accurate verification result can be obtained.

Second Embodiment

Next, a second embodiment of the present invention is explained. The second embodiment is different from the first embodiment in how to set an acceptable range of variation in a load loading curve in the setting process S2. Therefore, the explanation will be focused on this point. Constituents that are the same as in the first embodiment are indicated using the same reference numerals, and the explanation thereof is omitted.

Figure 7:
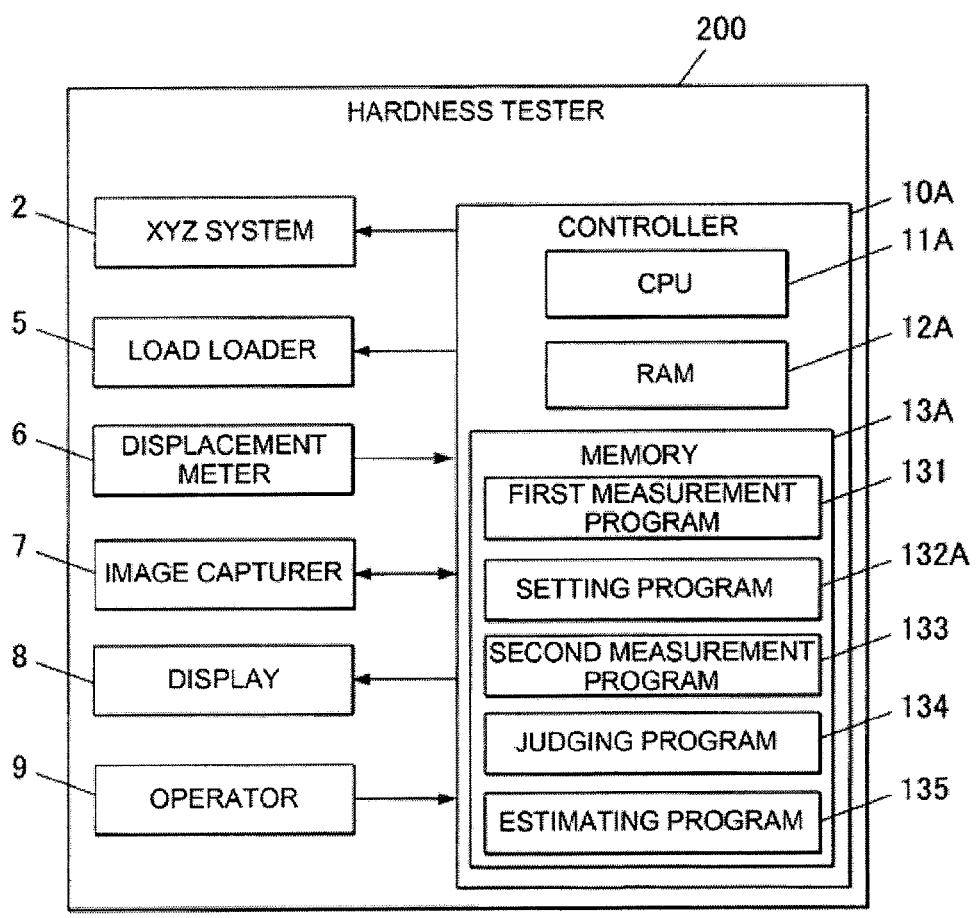
FIG. 7 is a block diagram illustrating a control configuration of a hardness tester according to a second embodiment.

As FIG. 7 illustrates, a hardness tester 200 according to the present embodiment includes a controller 10A. The controller 10A is configured to include a CPU 11A, a RAM 12A, a memory 13A, and the like.

The CPU 11A, for example, performs various control processes according to various processing programs for a hardness tester stored in the memory 13A. The RAM 12A, for example, includes a program storage area for deploying a processing program and the like executed by the CPU 11A; a data storage area storing input data and a processing result and the like generated when a processing program is executed; and the like.

The memory 13A, for example, stores the first measurement program 131, a setting program 132A, the second measurement program 133, the judging program 134, the estimating program 135, and the like.

Figure 8A:
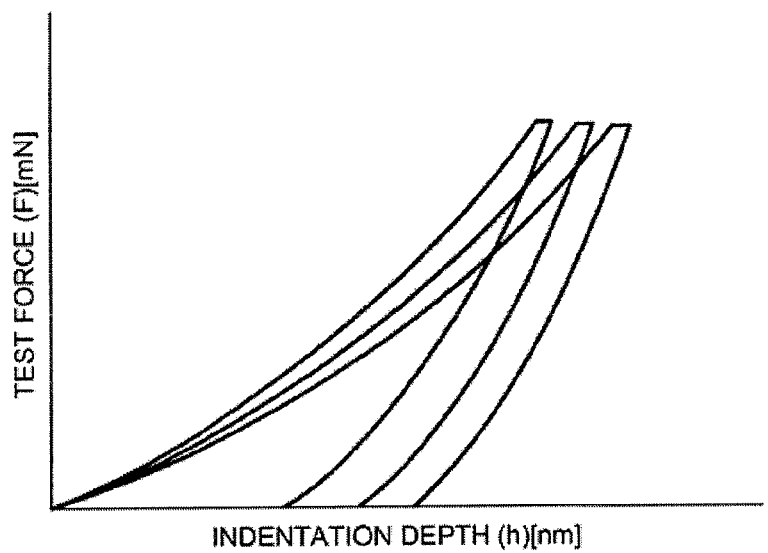
FIG. 8(a) is an example illustrating an indentation history curve measured by a first measurement process.
Figure 8B:
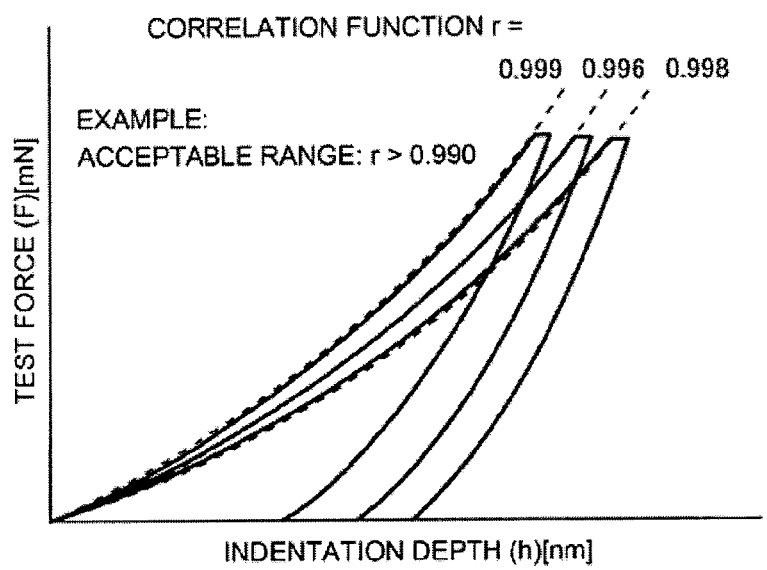
FIG. 8(b) is an example illustrating an acceptable range set by a setting process.

The setting program 132A, for example, is a program that causes the CPU 11A to set an acceptable range of variation in load loading history curves (load loading curves) based on the load loading history curves (load loading curves) of the plurality of the indentation history curves (indentation curves) obtained by executing the first measurement program 131. Specifically, first, the CPU 11A perceives the shape of the load loading history curves of the plurality of the indentation history curves obtained by executing the first measurement program 131. In the present embodiment, it is perceived that the load loading history curves are quadratic curves. Next, the CPU 11A fits the load loading curves of the plurality of the indentation curves (see FIG. 8(a)) obtained by executing the first measurement program 131 using quadratic functions to calculate a correlation coefficient (r), and sets the minimum of the calculated correlation coefficient (r) or above as an acceptable range of variation in a load loading curve (see FIG. 8(b)) (setting process). For example, as FIG. 8(b) illustrates, in a case where correlation coefficients (r) of three load loading curves are respectively 0.999, 0.996, and 0.998, the acceptable range can be set as r>0.990. At this time, it is also possible to multiply the calculated correlation coefficient by a safety factor to set an acceptable range of variation in load loading curves. For example, by performing an operation of a minimum correlation coefficient×½, an acceptable range is set. The safety factor is registered by a user in advance. By executing such a setting program 132A, the CPU 11A acts as a setter.

Figure 9A:
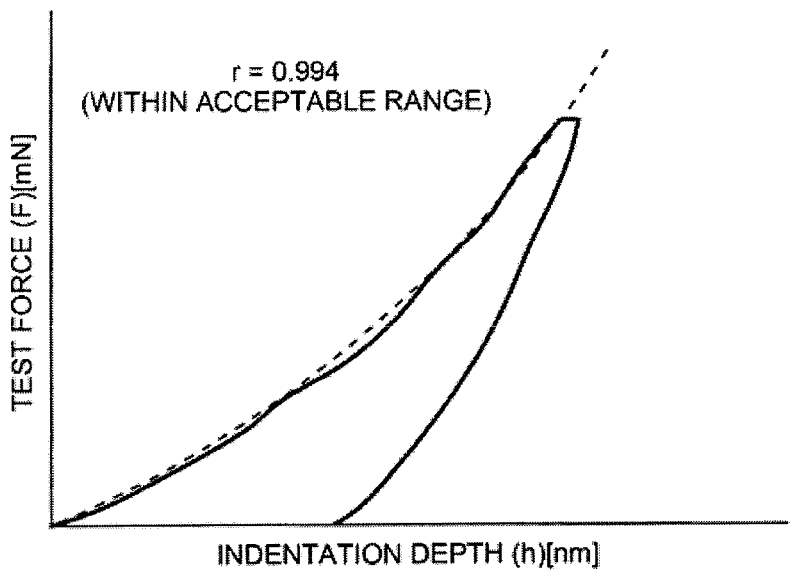
FIG. 9(a) is an example in which a load loading history curve measured in an actual usage environment is within an acceptable range.
Figure 9B:
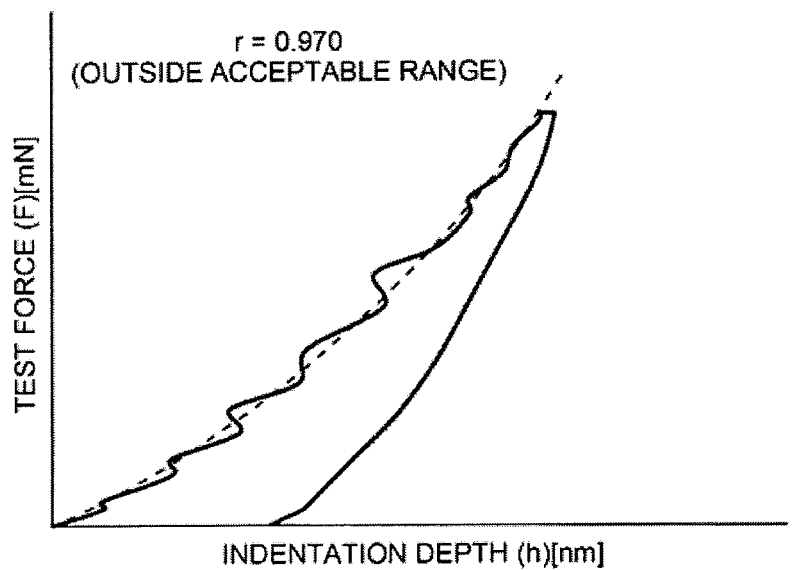
FIG. 9(b) is an example in which a load loading history curve measured in an actual usage environment is outside an acceptable range.

FIGS. 9(a) and 9(b) are each an example illustrating an indentation curve in a case where the second measurement process is performed after the setting process. FIG. 9(a) illustrates an example in which a load loading curve is within an acceptable range. FIG. 9(b) illustrates an example in which a load loading curve is outside an acceptable range. Similar to the first embodiment, in the case where a load loading curve is within an acceptable range, it is judged that the influence of disturbance is small; and in the case where a load loading curve is outside an acceptable range, it is judged that the influence of disturbance is large.

As described above, according to the present embodiment, the indenter 3 is a cone-shaped indenter. In the setting process (step S2), the load loading curves of the plurality of the indentation curves are fitted using quadratic functions to calculate a correlation coefficient, and the minimum of the calculated correlation coefficient or above is set as an acceptable range of variation in a load loading curve. Therefore, an acceptable range of variation in a load loading curve that can be used as a reference during a test in an actual usage environment is set based on a correlation coefficient calculated from the plurality of the load loading curves obtained from a test performed in a predetermined environment.

In the above described first and second embodiments, the judging process (step 4) and the estimation process (step S5) are explained as being executed by the CPU 11 or CPU 11A. However, these may also be performed by a user.

Further, in the above described first and second embodiments, it is also possible that the first measurement process (step S1) and the setting process (step S2) are performed by a manufacturer of the hardness tester at a factory of the hardness tester prior to shipment, and a set acceptable range is stored in the hardness tester. In this case, a user actually performing a hardness test executes from the second measurement process (step S3) to the estimation process (step S5) in a state in which the hardness tester is installed in actual usage environment, and, according to the results, verifies the influence and type of the disturbance in the actual usage environment.

Further, in the above described first and second embodiments, a case was explained as an example in which a cone-shaped (cone or pyramid) indenter was used as the indenter 3 and the load loading history curves were quadratic. However, as the indenter 3, besides this, it is also possible to use, for example, a ball indenter, a planer indenter, and the like. In this case, an acceptable range of variation in a load loading history curve may be set by fitting using a function having a shape that fits a load loading history curve of an indentation history curve.

It is noted that the foregoing examples have been provided merely for the purpose of explanation and are in no way to be construed as limiting of the present invention. While the present invention has been described with reference to exemplary embodiments, it is understood that the words which have been used herein are words of description and illustration, rather than words of limitation. Changes may be made, within the purview of the appended claims, as presently stated and as amended, without departing from the scope and spirit of the present invention in its aspects. Although the present invention has been described herein with reference to particular structures, materials and embodiments, the present invention is not intended to be limited to the particulars disclosed herein; rather, the present invention extends to all functionally equivalent structures, methods and uses, such as are within the scope of the appended claims.

The present invention is not limited to the above described embodiments, and various variations and modifications may be possible without departing from the scope of the present invention.

What is claimed is:

1. A hardness test method comprising:
a first measurement process comprising forming an indentation by pressing an indenter loaded with a predetermined load with respect to a test specimen for verification in a predetermined environment, and measuring, for a plurality of times under a same condition, an indentation history curve detecting an amount of displacement of the indenter and a test force loaded on the indenter during the formation of the indentation;
a setting process comprising:
setting a predetermined range of variation in load loading history curves based on load loading history curves, formed during load loading, of the plurality of the indentation history curves obtained by the first measurement process; and
fitting the load loading history curves of the plurality of the indentation history curves using a function having a shape that fits a load loading history curve of the plurality of the indentation history curves;
a second measurement process comprising measuring an indentation history curve under a same condition as the first measurement process with respect to the test specimen for verification in an actual usage environment; and
a judging process comprising judging whether a load loading history curve of the indentation history curve measured by the second measurement process is within the predetermined range of variation in a load loading history curve set by the setting process.

2. The hardness test method according to claim 1, the setting process further comprising:
selecting two curves having maximum and minimum slope values; and
setting a range between the two selected curves as the predetermined range of variation in the load loading history curve.

3. The hardness test method according to claim 2, wherein the slope values of the two selected curves are multiplied by a predetermined factor to set the predetermined range of variation in the load loading history curve.

4. The hardness test method according to claim 3 further comprising estimating a type of a disturbance in the actual usage environment based on the indentation history curve measured by the second measurement process.

5. The hardness test method according to claim 3, wherein the test specimen for verification is one of copper, aluminum and gold.

6. The hardness test method according to claim 2 further comprising estimating a type of a disturbance in the actual usage environment based on the indentation history curve measured by the second measurement process.

7. The hardness test method according to claim 2, wherein the test specimen for verification is one of copper, aluminum and gold.

8. The hardness test method according to claim 1, the setting process further comprising:
    calculating a correlation coefficient; and
    setting a minimum of the calculated correlation coefficient or above as the predetermined range of variation in the load loading history curve.

9. The hardness test method according to claim 8, wherein the minimum of the calculated correlation coefficient is multiplied by a predetermined factor to set the predetermined range of variation in the load loading history curve.

10. The hardness test method according to claim 9 further comprising estimating a type of a disturbance in the actual usage environment based on the indentation history curve measured by the second measurement process.

11. The hardness test method according to claim 9, wherein the test specimen for verification is one of copper, aluminum and gold.

12. The hardness test method according to claim 8 further comprising estimating a type of a disturbance in the actual usage environment based on the indentation history curve measured by the second measurement process.

13. The hardness test method according to claim 8, wherein the test specimen for verification is one of copper, aluminum and gold.

14. The hardness test method according to claim 1 further comprising estimating a type of a disturbance in the actual usage environment based on the indentation history curve measured by the second measurement process.

15. The hardness test method according to claim 14, wherein the test specimen for verification is one of copper, aluminum and gold.

16. The hardness test method according to claim 1, wherein the test specimen for verification is one of copper, aluminum and gold.

17. The hardness test method according to claim 1, wherein:
    the indenter is a cone-shaped indenter; and
    the function comprises quadratic functions.

18. At least one non-transitory computer readable medium that stores a set of executable instructions which, when executed by a processor, causes a computer to act as:
    a first scale configured to form an indentation by pressing an indenter loaded with a predetermined load with respect to a test specimen for verification in a predetermined environment, and further configured to measure for a plurality of times under a same condition an indentation history curve detecting an amount of displacement of the indenter and a test force loaded on the indenter during the formation of the indentation;
    a setter configured to:
        set a predetermined range of variation in load loading history curves based on the load loading history curves, formed during load loading, of the plurality of the indentation history curves obtained by the first scale; and
        fit the load loading history curves of the plurality of the indentation history curves using a function having a shape that fits a load loading history curve of the plurality of the indentation history curves;
    a second scale configured to measure an indentation history curve under a same condition as the first scale with respect to the test specimen for verification in an actual usage environment; and
    a judger configured to judge whether a load loading history curve of the indentation history curve measured by the second scale is within the predetermined range of variation in a load loading history curve set by the setter.

19. At least one computer for implementing a hardness test, comprising:
    a memory that stores a set of executable instructions for performing the hardness test; and
    a non-transitory processor;
        wherein the executable instructions, when executed by the processor, perform a first measurement procedure comprising forming an indentation by pressing an indenter loaded with a predetermined load with respect to a test specimen for verification in a predetermined environment, and measuring, for a plurality of times under a same condition, an indentation history curve detecting an amount of displacement of the indenter and a test force loaded on the indenter during the formation of the indentation;
        wherein the executable instructions, when executed by the processor, perform a setting procedure comprising:
            setting a predetermined range of variation in load loading history curves based on load loading history curves, formed during load loading, of the plurality of the indentation history curves obtained by the first measurement procedure; and
            fitting the load loading history curves of the plurality of the indentation history curves using a function having a shape that fits a load loading history curve of the plurality of the indentation history curves;
        wherein the executable instructions, when executed by the processor, perform a second measurement procedure comprising measuring an indentation history curve under a same condition as the first measurement procedure with respect to the test specimen for verification in an actual usage environment; and
        wherein the executable instructions, when executed by the processor, perform a judging procedure comprising judging whether a load loading history curve of the indentation history curve measured by the second measurement procedure is within the predetermined range of variation in a load loading history curve set by the setting procedure.

* * * * *